United States Patent
Hodgkinson et al.

(10) Patent No.: US 10,624,998 B2
(45) Date of Patent: *Apr. 21, 2020

(54) HYDROPHILIC MEDICAL DEVICES

(71) Applicant: Covidien LP, Mansfield, MA (US)

(72) Inventors: Gerald Hodgkinson, Guilford, CT (US); Ahmad Robert Hadba, Fort Worth, TX (US); Michael Prescott, Hamden, CT (US); Richard P. Stevenson, Colchester, CT (US); Arthur Hislop, Plantsville, CT (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/050,056

(22) Filed: Jul. 31, 2018

(65) Prior Publication Data

US 2018/0339087 A1 Nov. 29, 2018

Related U.S. Application Data

(62) Division of application No. 13/293,215, filed on Nov. 10, 2011, now abandoned.

(51) Int. Cl.
*A61B 17/072* (2006.01)
*A61L 15/26* (2006.01)
(Continued)

(52) U.S. Cl.
CPC ........ *A61L 31/14* (2013.01); *A61B 17/07292* (2013.01); *A61L 15/26* (2013.01);
(Continued)

(58) Field of Classification Search
CPC .... A61B 17/07292; A61B 2017/00004; A61B 2017/00942; A61F 2013/00221;
(Continued)

(56) References Cited

U.S. PATENT DOCUMENTS 3,729,007 A 4/1973 Mirkovitch
3,849,241 A 11/1974 Butin et al.
(Continued)

FOREIGN PATENT DOCUMENTS

EP 0331774 A1 9/1989
EP 2591813 A2 5/2013
(Continued)

OTHER PUBLICATIONS

Extended European Search Report from Application No. 12191922.9 dated Oct. 27, 2014.
(Continued)

*Primary Examiner* — Michael A Tolin
(74) *Attorney, Agent, or Firm* — Carter, DeLuca & Farrell LLP (57) ABSTRACT

A medical device including a plasma-treated porous substrate that is functionalized to provide a hydrophilic surface, and a process for preparing such a medical device, are disclosed. The method includes plasma treating at least a portion of a surface of a porous substrate with a gas species selected from oxygen, nitrogen, argon, and combination thereof. The gas species is configured to functionalize the surface of the medical device and form a hydrophilic surface.

2 Claims, 4 Drawing Sheets

(51) Int. Cl.
| | |
|---|---|
| *A61L 15/64* | (2006.01) |
| *A61L 31/06* | (2006.01) |
| *B29C 59/14* | (2006.01) |
| *D04H 1/56* | (2006.01) |
| *D04H 3/16* | (2006.01) |
| *A61L 31/14* | (2006.01) |
| *D06M 10/02* | (2006.01) |
| *A61B 17/00* | (2006.01) |
| *A61F 13/00* | (2006.01) |

(52) U.S. Cl.
CPC ............... *A61L 15/64* (2013.01); *A61L 31/06* (2013.01); *A61L 31/146* (2013.01); *A61L 31/148* (2013.01); *B29C 59/14* (2013.01); *D04H 1/565* (2013.01); *D04H 3/16* (2013.01); *D06M 10/025* (2013.01); *A61B 2017/00004* (2013.01); *A61B 2017/00942* (2013.01); *A61F 2013/00323* (2013.01); *A61L 2400/18* (2013.01); *B32B 2310/14* (2013.01); *Y10T 156/1052* (2015.01)

(58) Field of Classification Search
CPC . A61F 2013/00323; A61F 2013/00357; A61L 15/26; A61L 15/64; A61L 27/18; A61L 27/24; A61L 27/54; A61L 27/56; A61L 27/58; A61L 31/044; A61L 31/06; A61L 31/146; A61L 31/148; A61L 31/16; A61L 2400/18; B29C 59/14; B29C 2059/145; B29C 2059/147; B32B 2310/14; C08J 7/123; D04H 1/435; D04H 1/54; D04H 1/55; D04H 1/56; D04H 1/565; D04H 1/72; D04H 1/724; D04H 3/011; D04H 3/03; D04H 3/14; D04H 3/16; D06M 10/025

See application file for complete search history.

(56) References Cited

U.S. PATENT DOCUMENTS

| | | | |
|---|---|---|---|
| 5,236,563 | A | 8/1993 | Loh |
| 5,344,462 | A | 9/1994 | Paskalov et al. |
| 5,403,453 | A | 4/1995 | Roth et al. |
| 5,542,594 | A | 8/1996 | McKean et al. |
| 5,700,559 | A | 12/1997 | Sheu et al. |
| 6,063,105 | A | 5/2000 | Totakura |
| 6,165,217 | A | 12/2000 | Hayes |
| 6,203,564 | B1 | 3/2001 | Hutton et al. |
| 6,235,869 | B1 | 5/2001 | Roby et al. |
| 6,534,083 | B2 | 3/2003 | Gilding et al. |
| 7,294,357 | B2 | 11/2007 | Roby |
| 7,547,312 | B2 | 6/2009 | Bauman et al. |
| 7,604,668 | B2 | 10/2009 | Farnsworth et al. |
| 7,700,500 | B2 * | 4/2010 | Jordan .................. A61L 15/42 428/359 |
| 2002/0064875 | A1 | 5/2002 | Chen et al. |
| 2004/0127123 | A1 | 7/2004 | Jordan et al. |
| 2004/0166758 | A1 | 8/2004 | Reichmann et al. |
| 2006/0142797 | A1 | 6/2006 | Egnelov |
| 2007/0031470 | A1 | 2/2007 | Kladakis et al. |
| 2007/0060856 | A1 | 3/2007 | Spearman et al. |
| 2007/0150002 | A1 | 6/2007 | Szabo et al. |
| 2007/0198059 | A1 | 8/2007 | Patel et al. |
| 2008/0140115 | A1 | 6/2008 | Stopek |
| 2009/0162276 | A1 | 6/2009 | Martin et al. |
| 2009/0305024 | A1 | 12/2009 | Gvozdic |
| 2011/0045047 | A1 | 2/2011 | Bennett et al. |
| 2014/0079759 | A1 | 3/2014 | Patel et al. |

FOREIGN PATENT DOCUMENTS

| | | | |
|---|---|---|---|
| WO | 9513313 | A1 | 5/1995 |
| WO | 9618498 | A1 | 6/1996 |
| WO | 0145862 | A1 | 6/2001 |
| WO | 2006009925 | A2 | 1/2006 |

OTHER PUBLICATIONS

Extended European Search Report from Appl. No. 13189633.4 dated Oct. 27, 2014.
European Examination Report from Appl. No. EP 12191922.9 dated Mar. 14, 2017.
European Search Report for EP 12169360.0/1269 dated Jun. 15, 2012 (6 pages).
European Search Report from EP Application No. EP 11 00 7711, date of completion Nov. 4, 2011.
Mapili et al., "Laser-Layered Microfabrication of Spatially Patterned Functionalized Tissue-Engineering Scaffolds", J. Biomed Mater Res. B. Appl. Biomater, Nov. 2005, 75(2) pp. 414-424.
Connors et al., "Increase in wound breaking strength in rats in the presence of positively charged extra beads correlates with an increase in endogenous transforming growth factor-?R1 in close proximity to the wound", Wound Repair Regen., Jul.-Aug. 2000, 8(4), pp. 292-303.
Wan et al., Characterization of surface property of poly(lactide-co-glycolide) after oxygen plasma treatment, Biomaterials, Aug. 2004, 25(19), pp. 4777-4783.
de Leon et al., The Clinical Relevance of Treating Chronic Wounds with an Enhanced Near-Physiological Concentration of Platelet-Rich Plasma Gel, Adv. Skin Wound Care, Aug. 2011, 24(8), pp. 357-368.
Canadian Office Action issued in corresponding Appl. No. CA 2,794,238 dated Dec. 4, 2018 (4 pages).
Canadian Office Action issued in corresponding Appl. No. CA 2,794,238 dated Mar. 26, 2019 (4 pages).

* cited by examiner

HYDROPHILIC MEDICAL DEVICES

TECHNICAL FIELD

The present disclosure relates to medical devices, and more particularly, to surgical implants having a hydrophilic surface treatment for improved wettability and cellular attachment.

BACKGROUND

The use of medical devices, and more specifically, implants, is known. However, the implants, once placed in situ, may dislocate or migrate and, thus, are frequently secured to tissue during surgery using surgical tacking devices or fasteners, such as staples, clips, tacks, sutures, and the like. Porous implants are often utilized for their ability to provide biologic fixation and integration into surrounding tissue. The increased surface area of the implant allows for tissue infiltration into the implant via pores. The rate of tissue ingrowth is limited, however, and influenced by factors such as the porosity of the implant, depth of the porosity, and length of time of implantation.

It would be advantageous to provide an implant with improved fluid absorption and interaction with cells and biologic molecules. Such an implant would improve surgical site visibility during surgery by wicking away excess fluid, improve pooling of coagulation and growth factors near a wound site, and improve favorable host tissue interactions leading to infiltration and attachment of cell types important to wound healing.

SUMMARY

In accordance with aspects of the present disclosure, a method of making an absorbent surgical buttress, comprising: generating a plurality of fibers; collecting the plurality of fibers so that they adhere to one another and form a non-woven material; plasma treating at least a portion of a surface of the non-woven material with an ionizable gas species or combination of ionizable gas species configured to chemically modify or functionalize the surface of the non-woven material; and cutting the non-woven material into a desired shape for a surgical buttress.

The method can include ionizable gas species selected from the group consisting of air, water vapor, oxygen, nitrogen, argon, and combinations thereof. In certain embodiments, the fibers are melt extruded. The method of making the buttress can include blowing hot air at the fibers as they exit a die head and before they are collected. The hot air blown at the fibers can have a temperature greater than or equal to the melting temperature of the fibers. In certain embodiments, the fibers are collected as they cool.

In certain embodiments, the fibers are melt extruded from a polymer selected from the group consisting of lactide homopolymer, glycolide homopolymer, polydioxanone homopolymer, glycolide trimethylene carbonate copolymer, glycolide lactide copolymer, glycolide dioxanone trimethylene carbonate copolymer, and glycolide caprolactone trimethylene carbonate lactide copolymer.

In certain embodiments, the fibers are made from a bioabsorbable polymeric material. The melting temperature of the polymer may be between about 180 and about 250 degrees Celsius. In other embodiments, the melting temperature of the polymer is between about 80 degrees Celsius and about 190 degrees Celsius.

The hot air can have a temperature of between about 270 and about 290 degrees Celsius.

In certain embodiments, the fibers are collected on a conveyor surface. The method can include applying heat and pressure to the non-woven material before plasma treating the non-woven material.

In certain embodiments, the non-woven material is cut into a shape corresponding to the shape of a linear surgical stapler. In other embodiments, the non-woven material is cut into a shape corresponding to the shape of a circular surgical stapler.

The fibers can be generated by melt extruding a copolymer of glycolide, caprolactone, trimethylene carbonate and lactide having a melting temperature between about 140 degrees Celsius and about 185 degrees Celsius. The hot air blown at the fibers can have a temperature between about 185 degrees Celsius and about 195 degrees Celsius.

In certain embodiments, the fibers are generated by melt extruding dioxanone having a melting temperature between about 80 degrees Celsius and about 125 degrees Celsius. The air blown at the dioxanone fibers can have a temperature between about 145 degrees Celsius and about 155 degrees Celsius.

In a further aspect of the present disclosure, an absorbent surgical buttress comprises a non-woven material having a plurality of fibers adhered to one another, the fibers being formed from a melt extruded bioabsorbable polymeric material, the non-woven material being plasma treated on at least a portion of a surface of the non-woven material so that the surface is chemically modified or functionalized, the non-woven material being cut into a desired shape for the surgical buttress.

In certain embodiments, the fibers are formed from a polymeric material selected from the group consisting of lactide homopolymer, glycolide homopolymer, polydioxanone homopolymer, glycolide trimethylene carbonate copolymer, glycolide lactide copolymer, glycolide dioxanone trimethylene carbonate, and glycolide caprolactone trimethylene carbonate lactide.

The fibers may be formed from a polymeric material having a melting temperature of between about 180 and 250 degrees Celsius. In certain embodiments, the fibers are formed from a polymeric material having a melting temperature of between about 80 degrees Celsius and about 190 degrees Celsius In certain embodiments, the non-woven material is cut into a shape corresponding to the shape of a linear surgical stapler. In other embodiments, the non-woven material is cut into a shape corresponding to the shape of a circular surgical stapler.

BRIEF DESCRIPTION OF THE DRAWINGS

The foregoing objects and advantages of the disclosure will become more apparent from the reading of the following description in connection with the accompanying drawings, in which.

DETAILED DESCRIPTION

The present disclosure is directed to medical devices that have been chemically modified to render at least a surface of a substrate of the medical device more hydrophilic than its native state. In the case of porous devices, this surface treatment may enable the device to more quickly absorb and/or wick fluids, such as blood, interstitial fluid, cerebral spinal fluid, exudates, etc.

The following discussion includes a description of the presently disclosed medical device and an exemplary corresponding method of treating the same in accordance with the principles of the present disclosure. For the purposes of discussion, the medical device will be discussed in terms of a surgical buttress. However, those skilled in the art will appreciate the presently disclosed medical devices may be any surgical implant, such as meshes, scaffolds, grafts (e.g., fabrics and/or tubes), rings, sutures, patches, slings, pledgets, growth matrices, drug delivery devices, wound plugs, and, in general, soft tissue repair devices and surgical prostheses. In other embodiments, suitable medical devices may be topically applied medical products, such as wound dressings, coverings, gauzes, and the like, that can be used in medical/surgical procedures.

Figure 1:
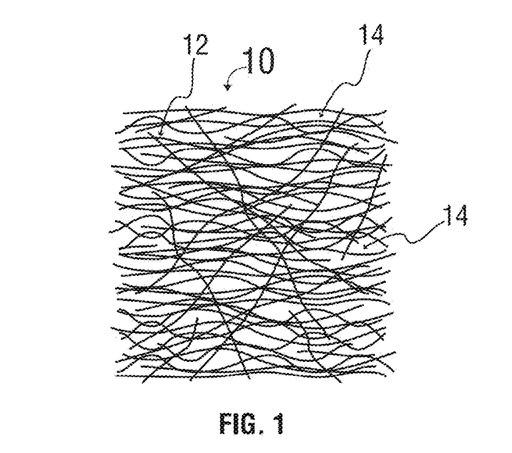
FIG. 1 is a perspective view of a surgical buttress in accordance with an embodiment of the present disclosure.

Referring now to the figures, wherein like components are designated by like reference numerals throughout the several views, FIG. 1 illustrates a surgical buttress 10, an example of a medical device in accordance with the present disclosure, including a porous substrate 12. Porous substrate 12 includes openings 14, such as pores, voids, or holes over at least a portion of a surface thereof. The openings of the buttress of the present disclosure may be sized to permit fibroblast through-growth and ordered collagen laydown, resulting in integration of the buttress into the body.

The openings may be present as a surface characteristic or a bulk material property, which partially or completely penetrates the substrate, and may be uniformly or randomly distributed across portions thereof. The buttress may have an open-cell structure, where the openings are connected to each other, forming an interconnected network. In such embodiments, the openings may be in sufficient number and size so as to interconnect across the entire thickness of the substrate. In some embodiments, the openings do not extend across the entire thickness of the porous substrate, but rather are present at a portion of the surface thereof. Conversely, the buttress may be closed cell, where the openings are not interconnected. Those skilled in the art reading the present disclosure may envision other distribution patterns and configurations of the openings in the porous substrate. It is envisioned that the substrate may, in embodiments, be partially or fully non-porous.

In embodiments, suitable materials for the porous substrate include, but are not limited to foams (e.g., open or closed cell foams). Where the porous substrate is a foam, the substrate may be formed using any method suitable to forming a foam or sponge including, but not limited to, lyophilization or freeze-drying of a composition. Suitable techniques for making foams are within the purview of those skilled in the art.

In embodiments, openings may be formed in filamentous buttresses via the spaces formed between the filaments of the buttress. Alternatively, the buttress may be formed from a continuous yarn that is arranged in loops that give rise to the openings in the buttress. The size of the openings between the filaments and spacing therebetween may vary depending on the surgical application and desired implant characteristics as envisioned by those skilled in the art.

The filaments may be made using any technique within the purview of those skilled in the art, such as, for example, extrusion, molding, and/or gel spinning. In embodiments, the filaments may be extruded through an extruder unit of a conventional type, such as those disclosed in U.S. Pat. Nos. 6,063,105, 6,203,564, and 6,235,869, the entire disclosures of each of which are incorporated by reference herein. In embodiments, filaments may be subsequently brought together into a group to form a yarn.

Once formed, a plurality of the filaments may then be braided, twisted, aligned, fused, entangled, intertwined, or otherwise joined or arranged to form a variety of different buttress shapes and sizes. In embodiments, the filaments may be drawn, oriented, crinkled, twisted, braided, commingled, or air entangled to form the buttress. The filaments may be woven, knitted, interlaced, braided, or formed into a buttress by non-woven techniques. The structure of the buttress will vary depending upon the assembling technique utilized to form the device, as well as other factors, such as the type of fibers used, the tension at which the fibers are held, and the mechanical properties required of the buttress.

In embodiments, knitting may be utilized to form a buttress of the present disclosure. Knitting involves, in embodiments, the intermeshing of filaments, or yarns thereof, to form loops or inter-looping of the filaments. In some embodiments, filaments may be warp-knitted thereby creating vertical interlocking loop chains and/or may be weft-knitted thereby creating rows of interlocking loop stitches across the buttress. In other embodiments, weaving may be utilized to form a buttress of the present disclosure. Weaving may include, in embodiments, the intersection of two sets of straight filaments, or yarns thereof, warp and weft, which cross and interweave at right angles to each other, or the interlacing of two filaments at right angles to each other. In some embodiments, the filaments may be arranged to form a net mesh which has isotropic or near isotropic tensile strength and elasticity.

In an embodiment, a nonwoven material is formed from lactide homopolymer, glycolide homopolymer, polydioxanone homopolymer, glycolide lactide copolymer, glycolide dioxanone trimethylene carbonate copolymer, glycolide caprolactone trimethylene carbonate lactide copolymer, or glycolide trimethylene carbonate copolymer. The polymer resin is melt extruded and the melt pump meters molten polymer into a die head. The melt pump speed is between about 2 and about 12 rpm. The polymer is forced through the array of holes in the die head, which has holes from about 0.13 mm diameter to about 0.3 mm diameter, in some embodiments, from about 0.175 mm diameter to about 0.25 mm diameter. The temperature at the die head is between about 200 degrees Celsius and about 275 degrees Celsius in some embodiments, from about 235 degrees Celsius and about 255 degrees Celsius in some embodiments, and the pressure at the head is between about 10 bar and about 80 bar. The polymer fibers exiting the die are forced onto a conveyor belt by blowing hot air. The hot air has a temperature of between about 230 degrees Celsius and about 325 degrees Celsius in some embodiments, and from about 265 degrees Celsius and about 295 degrees Celsius in some embodiments. The speed of the conveyor belt is between about 1 meter per minute and about 10 meters per minute. The fibers randomly land on the conveyor belt and build up to several layers in thickness. Suction is applied through the conveyor belt surface to help compact the fibers against each other as they cool. The material may be introduced into calendaring rolls to apply heat and pressure prior to being collected and staged. The material is then annealed to drive out any monomer and advance the crystallization of the polymer. Desirably, the material has a porosity of between about 50% and about 90%. The fiber diameters is between about 5 µm and about 100 µm. The material thickness is between about 150 µm and about 400 µm.

It is contemplated that the fibers can be generated at lower temperatures. In certain embodiments, fibers are formed from a polymer having a lower melting temperature. For example, a copolymer of glycolide, caprolactone, trimethylene carbonate and lactide could be melt extruded at between about 140 degrees Celsius and about 185 degrees Celsius. The hot air blown at the fibers has a temperature between about 185 degrees Celsius and about 195 degrees Celsius. In another example, dioxanone is melt extruded at between about 80 degrees Celsius and about 125 degrees Celsius. The hot air blown at the dioxanone fibers has a temperature between about 145 degrees Celsius and about 155 degrees Celsius. Thus, the buttress may formed from fibers melt extruded from polymers having a melting temperature of between about 80 degrees Celsius and about 190 degrees Celsius.

In embodiments, the filaments may be nonwoven and formed by mechanically, chemically, or thermally bonding the filaments, or yarns thereof, into a sheet or web in a random or systematic arrangement. For example, filaments may be mechanically bound by entangling the filaments to form the buttress by means other than knitting or weaving, such as matting, pressing, stitch-bonding, needlepunching, or otherwise interlocking the filaments to form a binderless network. In other embodiments, the filaments of the buttress may be chemically bound by use of an adhesive such as a hot melt adhesive, or thermally bound by applying a binder such as a powder, paste, or melt, and melting the binder on the sheet or web of filaments. In embodiments, the buttress may be spunbound and/or meltblown.

The diameter of the individual filaments may be from about 5 µm to about 100 µm, in embodiments, from about 10 µm to about 40 µm in some embodiments, and from about 15 µm to about 35 µm in some embodiments, and in some further embodiments, from about 18 µm to about 33 µm. The finished fabric thickness may be from about 150 µm to about 400 µm in embodiments, and from about 150 µm to about 300 µm in some embodiments, and from about 200 µm to about 250 microns in some embodiments, and in some further embodiments about 230 µm. The finished fabric weight may be from about 75 g/m$^2$ to about 100 g/m$^2$, in embodiments, from about 80 g/m$^2$ to about 95 g/m$^2$, and in some embodiments, about 87 g/m$^2$. It should be understood that different fabric thicknesses, weights, and porosities may be selected by varying manufacturing conditions.

The porous substrate may include any biocompatible natural or synthetic material. The material may be bioabsorbable or non-bioabsorbable. It should of course be understood that any combination of natural, synthetic, bioabsorbable and non-bioabsorbable materials may be used to form the porous substrate.

Suitable synthetic biodegradable materials include polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly(ortho esters), hydroxy alkanoates, tyrosine carbonates, poly(imide carbonates), poly(imino carbonates) such as poly (bisphenol A-iminocarbonate) and poly(hydroquinone-iminocarbonate), polyurethanes, polyanhydrides, polymer drugs (e.g., polydiflunisol, polyaspirin, and protein therapeutics), and copolymers and combinations thereof.

In embodiments, the porous substrate may be fabricated from a lactomer copolymer of glycolide and lactide derived from glycolic and lactic acids. In embodiments, the porous substrate may be fabricated from polyglyconate, a copolymer of glycolic acid and trimethylene carbonate.

In other embodiments, the porous substrate may be fabricated from a synthetic polyester composed of glycolide, dioxanone, and trimethylene carbonate. The polymer may include from about from about 50% to about 70% by weight glycolide, in embodiments, from about 55% to about 65% by weight glycolide, and in some embodiments, about 60% by weight glycolide; from about 4% to about 24% by weight dioxanone, in embodiments, from about 9% to about 19% by weight dioxanone, and in some embodiments, about 14% by weight dioxanone; and from about 16% to about 36% by weight trimethyl carbonate, in embodiments, from about 21% to about 31% by weight trimethyl carbonate, and in some embodiments, about 26% by weight trimethyl carbonate.

In yet other embodiments, the porous substrate may be fabricated from a copolymer of glycolide and trimethylene carbonate. The polymer may include from about 55% to about 75% by weight glycolide, in embodiments, about 60% to about 70% by weight glycolide, and in some embodiments, about 65% by weight glycolide, and from about 25% to about 45% by weight trimethylene carbonate, in embodiments, from about 30% to about 40% by weight trimethylene carbonate, and in some embodiments, about 35% by weight trimethylene carbonate.

In accordance with the present disclosure, the filaments and/or buttresses formed therefrom are chemically modified to render at least a portion of a surface of the filaments and/or buttress hydrophilic. The treatment process may render all, or most, surfaces of the substrate hydrophilic, including the surfaces of the openings or pores. In embodiments, about 25% to about 99% of the surfaces of the substrate are rendered hydrophilic, in some embodiments, about 40% to about 95% of the surfaces, and in some further embodiments, about 60% to about 90% of the surfaces. The treatment process does not require a secondary material to be coated or bound to the porous substrate to impart hydrophilicity, although in alternate embodiments, the chemical modification may result from the deposition of a coating material on the surface to render it more hydrophilic.

The chemical modification of the surface of the porous substrate may be by coronal discharge, low pressure plasma treatment, atmospheric plasma treatment, or other plasma technology systems. The treatment process functionalizes the surface of the substrate to render the surface more hydrophilic.

For example, in embodiments, a plasma treatment is used. The plasma may be formed of a single gas species such as oxygen, carbon dioxide, ammonia, nitrogen, or argon. The use of oxygen, for example, will result in surface activation of an oxygenate type, such as the formation of —OH, —CHO, and/or —COOH groups. It is envisioned that other gases, mixtures of gases, vapours of volatile organic molecules such as alcohols, water, or open air plasma may also be utilized. For example, ozone may be used in place of oxygen. In other examples, the plasma gas may be produced using an oxygen-containing molecule, a nitrogen-containing molecule, or mixtures thereof. In some embodiments, plasma gases may be used serially.

The surface of the substrate is modified with the addition of oxygen, other charged species, and/or hydrophilic moieties that will increase hydrostatic interactions both with water molecules and with hydrophilic domains of biologic molecules, such as proteins. In turn, undesirable hydrophobic interactions, such as protein hydrophobic domain bonding and loss of protein native structure, will be reduced at the substrate's surface, potentially minimizing adverse host inflammatory response.

Figure 2:
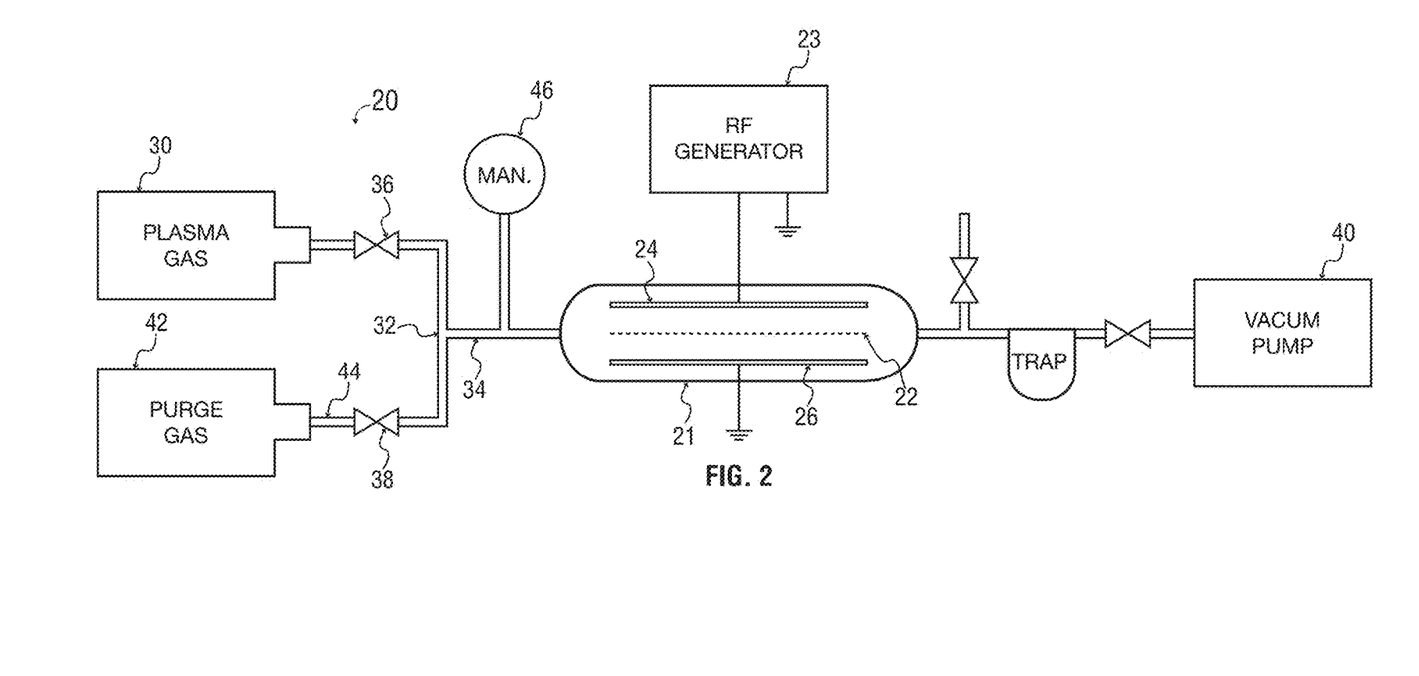
FIG. 2 is a schematic illustration of an apparatus which is suitable for carrying out plasma treatment of a substrate in accordance with the present disclosure.

An illustrative plasma treatment apparatus is shown in FIG. 2. Plasma treatment apparatus 20 includes a chamber 21 including a rack 22, such as a stainless steel rack, and a pair of parallel electrode plates 24 and 26 between which a plasma is formed, A radio frequency generator 23 is provided as a source of potential, with an output terminal of the generator 23 being connected to electrode plate 24 and electrode plate 26 being grounded, thereby providing means for generating an electrical field between the electrode plates 24 and 26, in which field the plasma can be created and sustained. To provide the desired gas from which the plasma is formed, the apparatus 20 includes a plasma gas source 30 (typically a standard gas cylinder) connected through a gas inlet system 32 to the chamber 21. The plasma gas source 30 includes a valve 36 for controlling the flow of gas through a supply line 34. A purge gas source 42, such as helium, is also connected through a line 44 and valve 38 to gas inlet system 32. A vacuum pump 40 is connected to the chamber 21 for reducing the gas pressure therein.

In a typical reaction, the porous substrate (for example, as depicted in FIG. 1) is mounted within the chamber 21 on the rack 22, positioned between electrode plates 24 and 26. Alternatively, the rack 22 may be movable so that the porous substrate may be pulled through the chamber 21. Alternatively, the porous substrate may travel through the plasma field between reels in a continuous reel to reel system requiring no support rack. The vacuum pump 40 is operated to reduce the pressure in the chamber 21. The gas inlet system 32 is operated to permit reacting gas monomer from plasma gas source 30 to flow into the chamber 21 through the supply line 34 before generating a plasma.

The plasma is created by applying the output of the radio frequency generator 23 to the electrode plate 24. The power supplied by the generator 23 is at the minimum required to sustain the plasma, as higher powered plasma will only degrade the surface of the substrate. The reaction between the plasma and the substrate is allowed to proceed for a period of time determined by the desired thickness and surface energy on the substrate and the concentration of gas monomers in the reacting vapor. The pressure within the chamber 21 is measured by a capacitance manometer 46 to maintain appropriate pressure throughout the reaction period.

Following the reaction period, the flow of gas from the plasma gas source 30 is terminated, the power from the generator 23 sustaining the plasma is turned off, and valve 38 is opened to permit gas to flow into the chamber 21 from purge gas source 42 to purge the substrate surface of highly reactive radicals which could cause premature contamination of the substrate's surface. Valve 38 is then closed, the chamber 21 is opened so that chamber 21 is returned to atmospheric pressure, and the plasma treated substrate is removed.

The plasma treated substrate may then be sterilized by any means within the purview of those skilled in the art including, but not limited to, ethylene oxide, electron beam, gamma irradiation, autoclaving, plasma sterilization, and the like.

It should be understood that the conditions under which treatment occurs may be dependent upon a number of factors, such as the type, size, thickness, and porosity of material being treated, the type and concentration of gas species being utilized and the flow rate thereof, the plasma technology system being utilized, and plasma treatment conditions such as voltage, pressure, temperature, duration, and the like.

For example, the plasma may include from about 1% to about 100% by weight of oxygen, nitrogen, or argon, in embodiments, from about 15% to about 90% by weight of oxygen, nitrogen, or argon, and in some embodiments, from about 25% to about 75% by weight oxygen, nitrogen, or argon. The gas may have a mass flow rate of from about 10 sccm to about 200 sccm, in embodiments, from about 25 sccm to about 150 sccm, and in some embodiments, about 50 sccm to about 100 sccm. The plasma generating electrodes may operate at a power of about 25 watts to about 1000 watts, in embodiments, from about 50 watts to about 750 watts, and in some embodiments, about 100 watts to about 500 watts. The treatment pressure may be about 25 mtorr to about 500 mtorr, in embodiments, from about 50 mtorr to about 400 mtorr, and in some embodiments, from about 100 mtorr to about 250 mtorr. The treatment may occur at a temperature of less than 100° C., and, in embodiments, at ambient temperature. The length of exposure may range from about 10 seconds to about 120 minutes, in embodiments, from about 30 seconds to about 60 minutes, and in some embodiments, from about 2 minutes to about 30 minutes. It will be appreciated by those skilled in the art that the treatment conditions may be outside the ranges set forth as discussed above.

In embodiments, the substrate treated in accordance with the present disclosure may also be subjected to a plasma polymerization process to form a polymer coating on at least a portion of the surface of the substrate. Such methods are disclosed, for example, in U.S. Pat. No. 7,294,357, the entire disclosure of which is incorporated herein by this reference.

The monomers used to form the polymer coating may be polymerized directly on the substrate's surface using plasma-state polymerization techniques generally known to those skilled in the art. In brief, the monomers are polymerized onto the surface of the substrate by activating the monomer in a plasma state. The plasma state generates highly reactive species, which form a highly cross-linked and highly-branched ultra-thin polymer coating, which is deposited on the surface of the substrate during plasma polymerization.

In embodiments, a suitable organic monomer or a mixture of monomers having polymerizable unsaturated groups is introduced into the chamber where it is fragmented and/or activated forming further excited species in addition to the activated plasma gases. The excited species and fragments of the monomer recombine upon contact with the substrate's surface to form a largely undefined structure which contains a complex variety of different groups and chemical bonds and forms a highly cross-linked polymer coating on the surface of the substrate. If oxygen, nitrogen, argon, or molecules possessing these elements are present, either within the plasma reactor during the polymer coating process or on exposure of the polymer coated substrate to oxygen or air subsequent to the plasma process, the polymeric deposit will include a variety of polar groups.

In embodiments, plasma polymerization may utilize solvents such as diglyme and tetraglyme, to produced PEG-like surfaces. In other embodiments, plasma polymerization may utilize fluorochemicals such as aliphatic fluorine-containing gases, to produced fluorinated polymer surfaces.

The amount and relative position of polymer deposition on the substrates are influenced by at least three geometric factors: (1) location of the electrode plates and distribution of charge; (2) monomer flow; and (3) substrate position within the chamber. In practice, an electric discharge from the RF generator may be applied to the electrode plates within the chamber and the selected monomers may be introduced into the chamber and energized into a plasma, saturating the space between the electrode plates with an abundance of energetic free radicals and lesser amounts of ions and free electrons produced by the monomers. As the substrate is passed through, or positioned between, the electrode plates, the surface of the substrate is bombarded with free radicals, resulting in the formation of the polymer coating.

In embodiments, siloxane monomers with hydrophilic end groups may be used in the plasma polymerization process to produce polymer coatings on the substrate's surface. In some embodiments, aliphatic hydrocyclosiloxane monomers, alone or mixed with co-monomers, may be utilized to provide polymer coatings having a homogenous or mixed property coating. For example, by introducing reactive functionalizing monomers, organo-based monomers, or fluorocarbon monomers together with the aliphatic hydrocyclosiloxane monomers in the plasma polymerization system, physical pore size and chemical affinity of the plasma copolymerized aliphatic hydrocyclosiloxane coating with selective monomers can be controlled. This allows the use of the copolymerized plasma polymer coating for applications which require the coating to differentiate between certain types of gases, ions, and molecules and it also may be utilized to introduce functional groups to the polymer coating which, in turn, can help link hydrophilic molecules to the polymer coating.

The openings in the substrate may be partially or completely filled with filler material, such as uncrosslinked molecules, hydrogels, absorbable polymer spheres, or interpenetrating chemically or ionically crosslinked hydrogels. In embodiments, the filler material may fill about 5% to about 100% of the openings in the substrate, in some embodiments, about 10% to about 80% of the openings, and in some other embodiments, from about 25% to about 75% of the openings. The filler material may be incorporated into the buttress during fabrication, prior to plasma treatment, and/or may be incorporated into the substrate after plasma treatment.

The structure of the porous substrate provides the infrastructure for the buttress or other medical device formed thereof and the filler material may provide a reservoir for the delivery of drugs or other factors from the substrate and/or a repository of protein, cell, or growth factor recruiting moieties that encourage tissue healing or cell growth when the medical device is implanted within the body.

For example, hydrogels may be used as a means to absorb blood and as carriers of thrombogenic agents for blood clotting and hemostasis at wound sites. Hydrogels can be modified with any number of conjugated molecules such as cell adhesion proteins, growth factors, peptides, and endogenous growth factor capturing molecules, such as heparin sulfate, to promote tissue ingrowth and healing. In embodiments, the filler material may include releasable factors that have an associated binding interaction that will release agents by unbinding and diffusion, or filler material degradation.

Examples of filler materials which may be utilized in accordance with the present disclosure for example, include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of filler materials may be used.

Other filler materials include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins; cytotoxic drugs; chemotherapeutics, estrogens; antibacterials; antibiotics; anti-fungals; anti-virals; anticoagulants; anticonvulsants; antidepressants; antihistamines; and immunological agents.

Examples of yet other suitable filler materials include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Figure 3A:
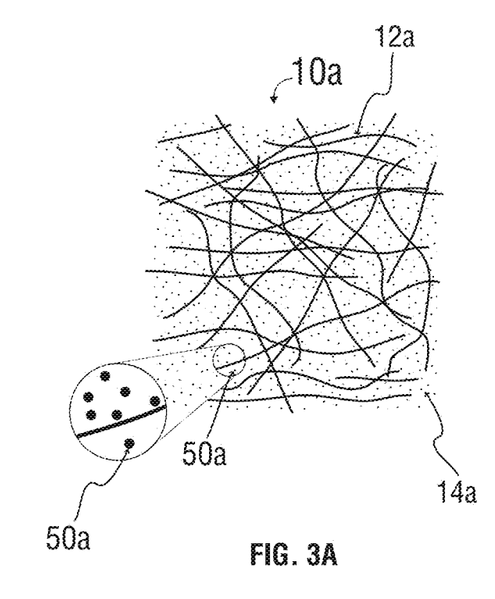
FIGS. 3A-3C are cross-sectional views of the surgical buttress of FIG. 1, possessing filler materials in accordance with embodiments of the present disclosure.

As illustrated in FIG. 3A, the filler material 50a may be non-crosslinked molecules which are embedded within the openings 14a of the substrate 12a of the buttress 10a by conventional methods within the purview of those skilled in the art, such as by solvent solution impregnation and subsequent solvent evaporation. Examples of non-crosslinked molecules which may be included with the above fillers include, for example, high molecular weight PEG, polyalkylene oxides such as PLURONICS, PEG-poly(alpha-hydroxy esters) block copolymers, poly(vinyl pyrrolidone), poly(vinyl alcohol), polyacrylates and polyacrylate copolymers, such as poly(acrylic acid), poly(methacrylic acid), poly(sodium acrylate), poly(2-hydroxyethyl methacrylate), poly(potassium sulfopropyl acrylate) and their copolymers, dextran, alginate, carboxymethyl cellulose, chitosan, hyaluronic acid, fibrin, gelatin, collagen, laminin, oxidized cellulose, and combinations thereof.

Figure 3B:
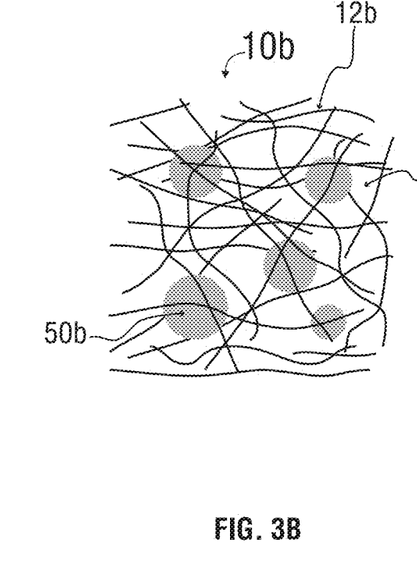

FIG. 3B illustrates a buttress 10b including a plurality of filler material 50b in the form of beads. The beads 50b may be incorporated into and/or onto at least a portion of the openings 14b of the substrate 12b in a systematic or random distribution pattern. In embodiments, the filler material 50b itself may be shaped and formed into a bead 50b. Alternatively, each bead may include a casing (not shown) made from a degradable polymeric material which defines a core containing a quantity of filler material 50b therein. The beads 50b may be entrapped within the buttress 10b so that they may be delivered and held at the tissue site without appreciable bead migration. In embodiments, the beads 50b may be blown onto, or laid into, the openings 14b of the substrate 12b during buttress fabrication as filaments are being deposited on a target surface so that the beads 50b are trapped between filaments as intrafiber bonds form. Beads 50b may be formed from hydrogels composed of PEG based polymers, dextran, pHEMA, carboxymethyl cellulose, or alginate, for example. Other materials for forming beads include, for example, polyalpha-hydroxy esters) configured as single or multilayered beads. In some embodiments, charged dextran beads may be incorporated into buttress 10b. It is envisioned that a variety of beads may be incorporated into a buttress 10b of the present disclosure.

Figure 3C:
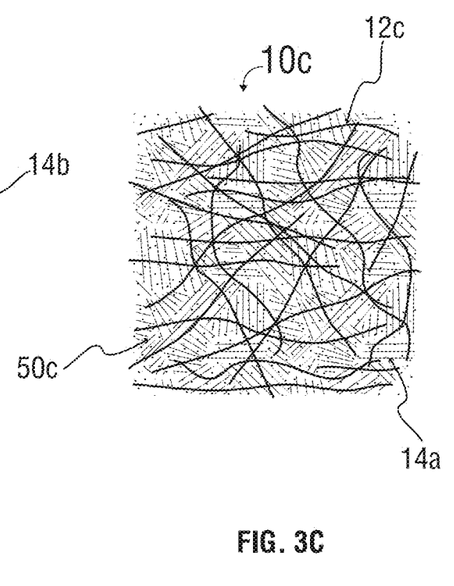

FIG. 3C illustrates a buttress 10c including an interpenetrating network of filler material 50c. In embodiments, the openings 14c of the porous substrate 12c is impregnated with hydrogel precursors which are crosslinked to form the interpenetrating network 50c throughout the buttress 10c. Hydrogel precursors include, for example, PEG poly(alpha-hydroxy esters) block copolymers, hyaluronic acid, collagen, and alginate.

The following non-limiting example illustrates the improved wettability of substrates formed in accordance with the present disclosure.

EXAMPLES

Example 1

A nonwoven material was formed from a glycolide trimethylene carbonate copolymer, having a melting temperature of approximately 215 degrees Celsius. The polymer resin was melt extruded at a temperature of between about 180 and about 250 degrees Celsius. A melt pump metered the molten polymer into a die head. The polymer melt was forced through an array of holes in the die head. Various die head types have hole configurations ranging from 0.13 to 0.25 min in diameter. The temperature at the die head was about 240 degrees Celsius at a head pressure of approximately 30 bar, depending on die head type. The polymer fibers exiting the die were forced onto a moving conveyor belt by means of compressed/blown hot air. The hot air had a temperature of between about 270 degrees Celsius and about 290 degrees Celsius, which is hotter than the melt temperature of the polymer. The conveyor belt speed was about 8 meters per minute. The fibers randomly landed on the conveyor belt and built up to several layers in thickness. Suction was applied through the conveyor belt surface to help compact the fibers against each other as they cooled. The material was then introduced into a calendaring roll device which heated and compressed the fabric material i.e., enhancing the polymer state of crystallization and thickness uniformity. The material was then collected and stored. In a subsequent process the material was annealed at a temperature of about 120 Celsius to remove residual monomers and to allow any crystallization potential of the polymer to complete. Individual fiber diameters ranged from 5 μm to 30 μm. The resulting material has a porosity of about 50% to about 90%. The material thickness was about 230 μm. The material was then plasma treated.

Example 2

A first set of nonwoven buttresses, set A, were formed from a copolymer of glycolic acid and trimethylene carbonate. A second set of nonwoven buttresses, set B, were formed from a copolymer of glycolide (65%) and trimethylene carbonate (35%). The fibers of each buttress defined interconnected openings that extended throughout the buttress in a tortuous path. One buttress from each set was left untreated while a second buttress was plasma treated for 5 minutes at 500 Watts in a single gas atmosphere.

Figure 4:
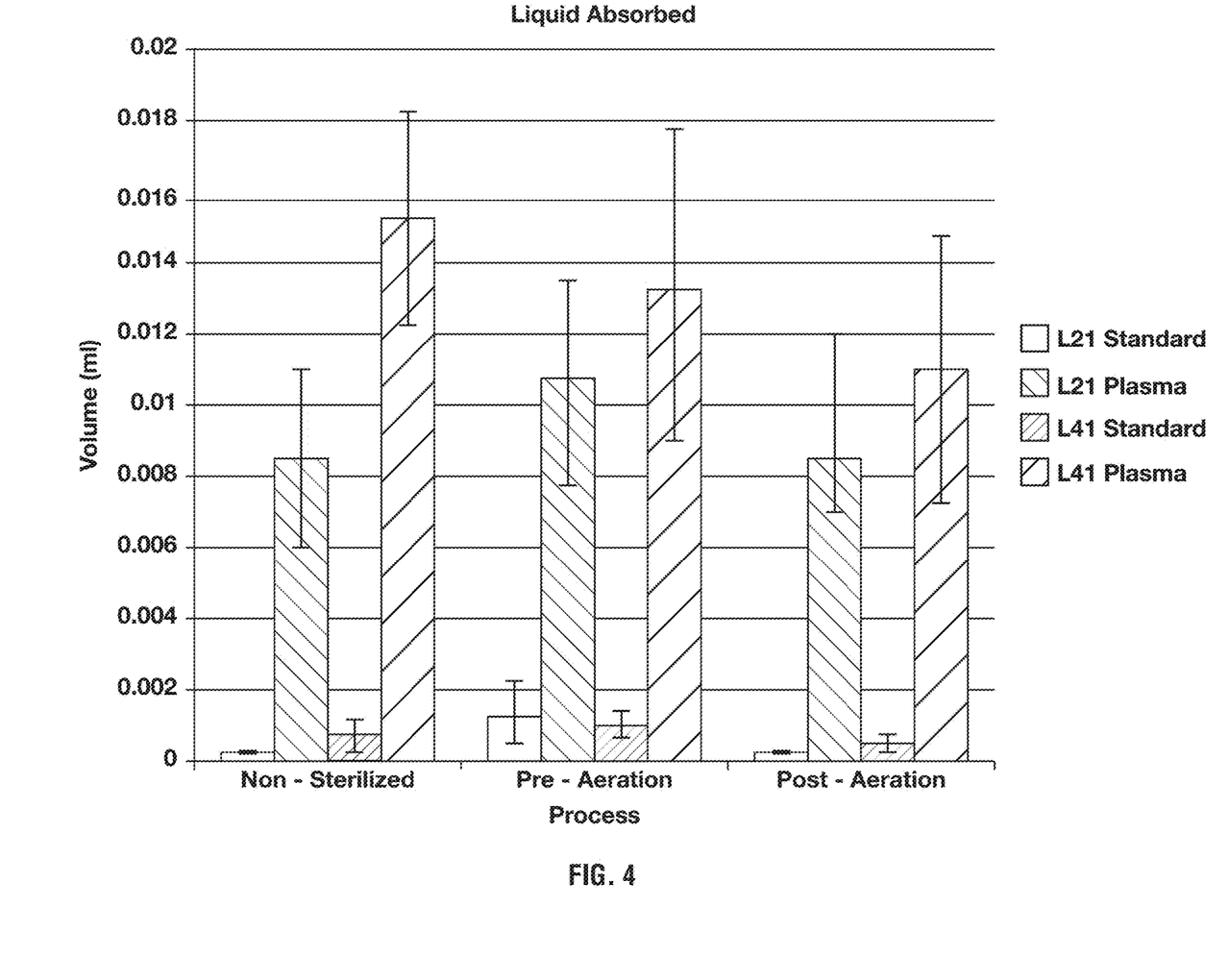
FIG. 4 is a graph illustrating a comparison of liquid absorbance of untreated surgical buttresses and plasma treated surgical buttresses formed in accordance with an embodiment of the present disclosure.
Figure 5:
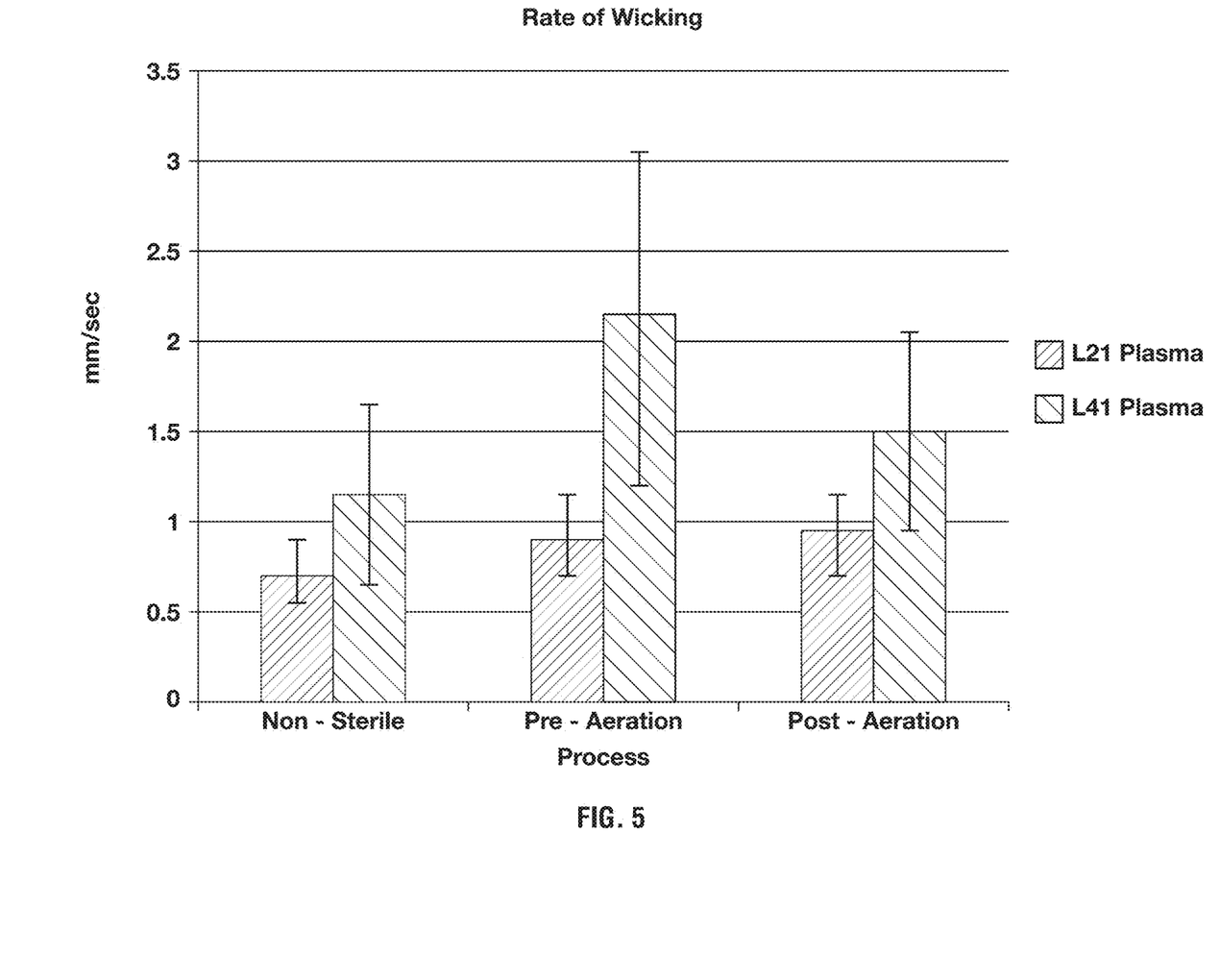
FIG. 5 is a graph illustrating a comparison of the rate of wicking of the plasma treated surgical buttresses of FIG. 4.

An outer edge of each buttress was held in a pool of dyed albumin solution used to simulate blood, to both observe and measure liquid absorption by the buttresses. Results for each buttress are provided in FIG. 4. As shown in FIG. 4, the plasma treated buttresses provided greater liquid absorbance. The rate of wicking of each of the plasma treated buttresses is illustrated in FIG. 5.

The present disclosure also incorporates aspects described in the following numbered paragraphs.

1. A method of making an absorbent surgical buttress, comprising: generating a plurality of fibers; collecting the plurality of fibers so that they adhere to one another and form a non-woven material; plasma treating at least a portion of a surface of the non-woven material with an ionizable gas species or combination of ionizable gas species configured to chemically modify or functionalize the surface of the non-woven material; and cutting the non-woven material into a desired shape for a surgical buttress.

2. The method of making an absorbent surgical buttress according to claim 1, wherein the ionizable gas species is selected from the group consisting of air, water vapor, oxygen, nitrogen, argon, and combinations thereof.

3. The method of making an absorbent surgical buttress according to any one of paragraphs 1 through 2, wherein the fibers are melt extruded.

4. The method of making an absorbent surgical buttress according to any one of paragraphs 1 through 3, further comprising blowing hot air at the fibers as they exit a die head and before they are collected.

5. The method of making an absorbent surgical buttress according to any one of paragraphs 1 though 4, further comprising blowing hot air at the fibers as they exit the die head and before they are collected, the hot air having a temperature greater than or equal to the melting temperature of the fibers.

6. The method of making an absorbent surgical buttress according to any one of paragraphs 1 though 5, wherein the fibers are collected as they cool.

7. The method of making an absorbent surgical buttress according to any one of paragraphs 1 through 6, wherein the fibers are melt extruded from a polymer selected from the group consisting of lactide homopolymer, glycolide homopolymer, polydioxanone homopolymer, glycolide trimethylene carbonate copolymer, glycolide lactide copolymer, glycolide dioxanone trimethylene carbonate copolymer, and glycolide caprolactone trimethylene carbonate lactide copolymer.

8. The method of making an absorbent surgical buttress according to any one of paragraphs 1 through 7, wherein the fibers are made from a bioabsorbable polymeric material.

9. The method of making an absorbent surgical buttress according to any one of paragraph 1 through 8, wherein the melting temperature of the polymer is between about 180 and about 250 degrees Celsius.

10. The method of making an absorbent surgical buttress according to any one of paragraphs 1 through 9, wherein the melting temperature of the polymer is between about 80 degrees Celsius and about 190 degrees Celsius.

11. The method of making an absorbent surgical buttress according to any one of paragraphs 1 through 10, wherein the hot air has a temperature of between about 270 and about 290 degrees Celsius.

12. The method of making an absorbent surgical buttress according to any one of paragraphs 1 through 11, wherein the fibers are collected on a conveyor surface.

13. The method of making an absorbent surgical buttress according to any one of paragraphs 1 through 12, further comprising applying heat and pressure to the non-woven material before plasma treating the non-woven material.

14. The method of making an absorbent surgical buttress according to any one of paragraphs 1 through 13, wherein the non-woven material is cut into a shape corresponding to the shape of a linear surgical stapler.

15. The method of making an absorbent surgical buttress according to any one of paragraphs 1 through 14, wherein the non-woven material is cut into a shape corresponding to the shape of a circular surgical stapler.

16. The method of making an absorbent surgical buttress according to any one of paragraphs 1 through 15, wherein the fibers are generated by melt extruding a copolymer of glycolide, caprolactone, trimethylene carbonate and lactide having a melting temperature between about 140 degrees Celsius and about 185 degrees Celsius.

17. The method of making an absorbent surgical buttress according to any one of paragraphs 1 through 16, wherein the hot air blown at the fibers has a temperature between about 185 degrees Celsius and about 195 degrees Celsius.

18. The method of making an absorbent surgical buttress according to any one of paragraphs 1 through 17, wherein the fibers are generated by melt extruding dioxanone having a melting temperature between about 80 degrees Celsius and about 125 degrees Celsius.

19. The method of making an absorbent surgical buttress according to any one of paragraphs 1 through 18, wherein the air blown at the dioxanone fibers has a temperature between about 145 degrees Celsius and about 155 degrees Celsius 20. An absorbent surgical buttress, comprising a non-woven material having a plurality of fibers adhered to one another, the fibers being formed from a melt extruded bioabsorbable polymeric material, the non-woven material being plasma treated on at least a portion of a surface of the non-woven material so that the surface is chemically modified or functionalized, the non-woven material being cut into a desired shape for the surgical buttress.

21. The absorbent surgical buttress according to paragraph 20, wherein the fibers are formed from a polymeric material selected from the group consisting of lactide homopolymer, glycolide homopolymer, polydioxanone homopolymer, glycolide trimethylene carbonate copolymer, glycolide lactide copolymer, glycolide dioxanone trimethylene carbonate, and glycolide caprolactone trimethylene carbonate lactide.

22. The absorbent surgical buttress according to any one of paragraphs 20 through 21, wherein the fibers are formed from a polymeric material having a melting temperature of between about 180 and 250 degrees Celsius.

23. The absorbent surgical buttress according to any one of paragraphs 20 through 22, wherein the fibers are formed from a polymeric material having a melting temperature of between about 80 degrees Celsius and about 190 degrees Celsius 24. The absorbent surgical buttress according to any one of paragraphs 20 through 23, wherein the non-woven material is cut into a shape corresponding to the shape of a linear surgical stapler.

25. The absorbent surgical buttress according to any one of paragraphs 20 through 24, wherein the non-woven material is cut into a shape corresponding to the shape of a circular surgical stapler.

26. A method of preparing a medical device having a hydrophilic surface, the method comprising: plasma treating at least a portion of a surface of a porous medical device with a gas species selected from the group consisting of oxygen, nitrogen, argon, and combinations thereof, the gas species being configured to functionalize the surface of the medical device and form a hydrophilic surface.

27. The method of paragraph 26, wherein plasma treating comprises: placing the medical device within a chamber between a pair of electrode plates; releasing the gas species into the chamber; and generating an electrical field between the pair of electrode plates to sustain a plasma.

28. The method of paragraph 27, wherein plasma treating further comprises: terminating the flow of the gas species into the chamber; and purging the surface of the medical device with an inert gas.

29. The method of any one of paragraphs 26 through 28, further comprising sterilizing the plasma treated medical device.

30. The method of any one of paragraphs 26 through 29, further comprising introducing a filler material into openings of the medical device.

31. The method of any one of paragraphs 26 through 30, further comprising coating at least a portion of the surface of the medical device with monomers including hydrophilic end groups.

32. The method of any one of paragraphs 26 through 31, further comprising polymerizing at least a portion of the surface of the medical device with functionalizing monomers by introducing the monomers into the chamber with the gas species.

33. A medical device comprising a plasma-treated porous substrate that is functionalized to provide a hydrophilic surface, the porous substrate including a filler material embedded within at least a portion of openings therein.

34. The medical device of paragraph 33, wherein the substrate is selected from the group consisting of buttresses, meshes, scaffolds, grafts, rings, sutures, patches, slings, pledgets, growth matrices, drug delivery devices, wound plugs, soft tissue repair devices, surgical prostheses, wound dressings, coverings, and gauzes.

35. The medical device of any one of paragraph 33 and 34, wherein the substrate is fabricated from a synthetic biodegradable polymer.

36. The medical device of any one of paragraphs 33 through 35, wherein the synthetic biodegradable polymer is selected from the group consisting of lactide, glycolide, caprolactone, trimethyl carbonate, dioxanone, and copolymers and combinations thereof.

37. The medical device of any one of paragraphs 33 through 36, wherein the substrate is fibrous and includes openings formed between fibers thereof.

38. The medical device of any one of paragraphs 33 through 37, wherein the substrate is nonwoven.

39. The medical device of any one of paragraphs 33 through 38, wherein the filler material is selected from the group consisting of uncrosslinked molecules, hydrogels, absorbable polymer spheres, interpenetrating chemically or ionically crosslinked hydrogels, and combinations thereof.

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision many other possible variations that are within the scope and spirit of the present disclosure.

What is claimed is:

1. A method of making an absorbent surgical buttress, comprising:
    generating a plurality of fibers by melt extruding a copolymer of glycolide, caprolactone, trimethylene carbonate and lactide having a melting temperature between about 140° C. and about 185° C., wherein the plurality of fibers are melt extruded from a die head;
    blowing hot air at the plurality of fibers as they exit the die head;
    collecting the plurality of fibers so that they adhere to one another and form a non-woven material;
    plasma treating at least a portion of a surface of the non-woven material with an ionizable gas species or combination of ionizable gas species configured to chemically modify or functionalize the surface of the non-woven material; and
    cutting the non-woven material into a desired shape for a surgical buttress.

2. The method of making an absorbent surgical buttress according to claim 1, wherein the hot air blown at the plurality of fibers has a temperature between about 185° C. and about 195° C.

* * * * *